United States Patent [19]

Itoh

[11] Patent Number: 5,445,037
[45] Date of Patent: Aug. 29, 1995

[54] SAMPLE SORTING APPARATUS

[76] Inventor: Teruaki Itoh, 5-25, Kokaihonmachi, Kumamoto-shi, Kumamoto-ken 860, Japan

[21] Appl. No.: 183,742

[22] Filed: Jan. 21, 1994

[30] Foreign Application Priority Data

Jan. 29, 1993 [JP] Japan .................. 5-013295

[51] Int. Cl.⁶ ........................................ G01N 35/02
[52] U.S. Cl. .................................... 73/864.25
[58] Field of Search ........... 73/863.01, 864.23–864.25; 198/437, 457, 810; 422/63–65

[56] References Cited

U.S. PATENT DOCUMENTS 3,764,268 10/1973 Kosowsky et al. .................. 422/64
4,863,690 9/1989 Berthold et al. .

FOREIGN PATENT DOCUMENTS 0243915 11/1987 European Pat. Off. .
1381514 1/1975 United Kingdom .

Primary Examiner—Robert Raevis
Attorney, Agent, or Firm—Nixon & Vanderhye

[57] ABSTRACT

A sample sorting apparatus includes a first conveying means for conveying a parent sample vessel along a first convey path, a means for taking up a parent sample from the parent sample vessel conveyed by the first conveying means, a sample recognition information reading means for reading sample recognition information attached to the parent sample vessel, a second conveying means for conveying child sample vessels along a second convey path, and a means, provided to the second convey path, for distributing the parent sample took up by the taking up means into a number of child sample vessels in accordance with the read sample recognition information.

14 Claims, 4 Drawing Sheets

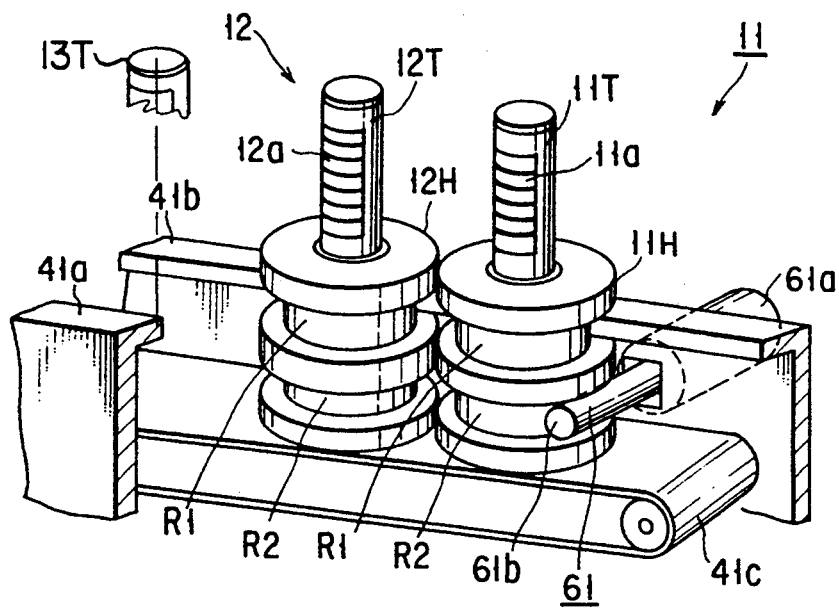
FIG. 2
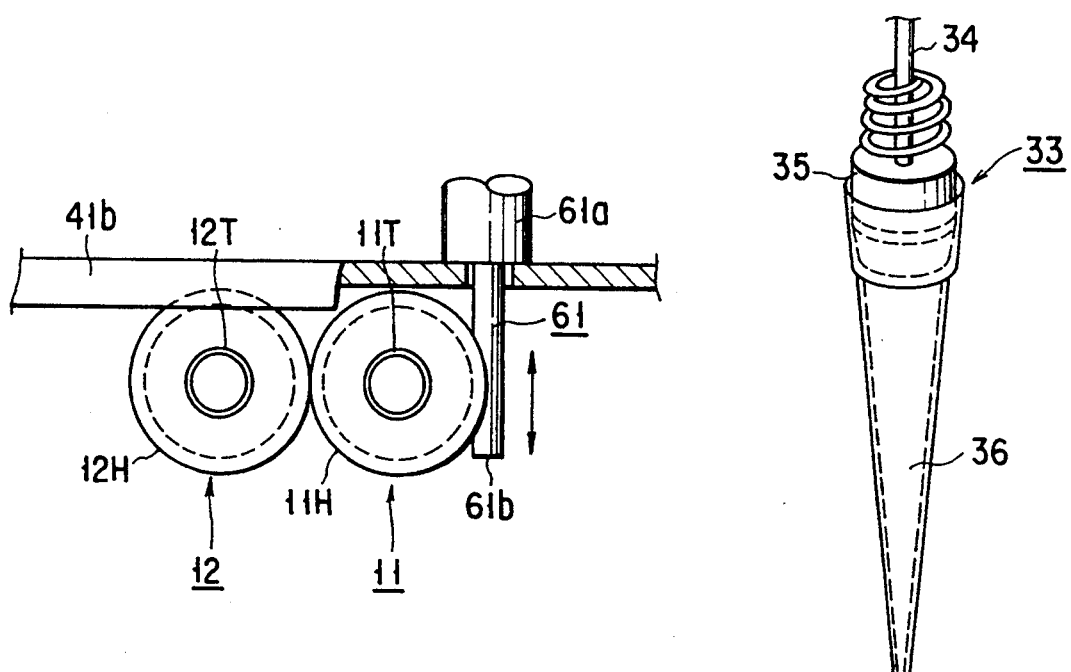
FIG. 3
FIG. 4

SAMPLE SORTING APPARATUS

BACKGROUND OF THE INVENTION

1. Field of the Invention

The present invention relates to a sample sorting apparatus for taking up a parent sample from a parent sample vessel containing a sampled liquid (to be referred to as a "parent sample" hereinafter), e.g., blood, and distributing a predetermined amount of the took up parent sample as a sample (to be referred to as a "child sample" hereinafter) to be subjected to various types of inspection and analysis to a child sample vessel.

2. Description of the Related Art

Generally, when a parent sample is to be took up from a test tube serving as a parent sample vessel and be distributed to other plurality of test tubes serving as child sample vessels, a batch type sample sorting apparatus (taking up/distributing apparatus) is used. With this sample sorting apparatus, the parent sample took up from the test tube serving as the parent sample vessel is distributed to a preset number of (e.g., five) empty test tubes in a predetermined amount, and the test tubes containing the distributed parent sample are transported by a transporting means to a position where various types of inspection and analysis are performed.

However, this batch type sample sorting apparatus can only distribute all the parent samples to correspond to a predetermined number of (e.g., five) inspection items. Hence, when the respective parent samples are to be distributed to correspond to different numbers of inspection items, sometimes the number of test tubes for storing the child sample is excessive or short. Therefore, the processing efficiency is degraded.

SUMMARY OF THE INVENTION

The present invention has been made to cope with the above situation, and has as its object to provide a sample sorting apparatus that can efficiently and accurately perform distribution even when the respective parent samples are to be distributed to correspond to different numbers of inspection items.

It is another object of the present invention to provide a more efficient sample sorting system by coupling sample sorting apparatuses.

According to the present invention, there is provided a sample sorting apparatus comprising first conveying means for conveying a parent sample vessel containing a parent sample along a first convey path; means for taking up the parent sample from the parent sample vessel conveyed by the first conveying means; sample recognition information reading means for reading sample recognition information attached to the parent sample vessel; second conveying means for conveying child sample vessels along a second convey path; and means for distributing the parent sample dispensed by the taking up means into child sample vessels conveyed by the second conveying means in accordance with the sample recognition information read by the reading means.

According to the sample sorting apparatus of the present invention, even when the respective parent samples are to be distributed to correspond to, e.g., different numbers of inspection items, an efficient distributing operation can be accurately performed. Even when samples sorting apparatuses are operated simultaneously, the loads of the respective apparatuses can be uniformed, thereby decreasing occurrence of a failure. Furthermore, even if one apparatus breaks down, the entire system need not be stopped, so that continuous operation can be performed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a perspective view of a transport lane, sample conveying bodies, and a stopper of the sample sorting apparatus according to the first embodiment of the present invention;

FIG. 3 is a plan view of the transport lane, the sample conveying bodies, and the stopper of the sample sorting apparatus according to the first embodiment of the present invention;

FIG. 4 is a perspective view showing the suction tool of the sample sorting apparatus according to the first embodiment of the present invention;

DETAILED DESCRIPTION OF THE PREFERRED EMBODIMENTS

Figure 1:
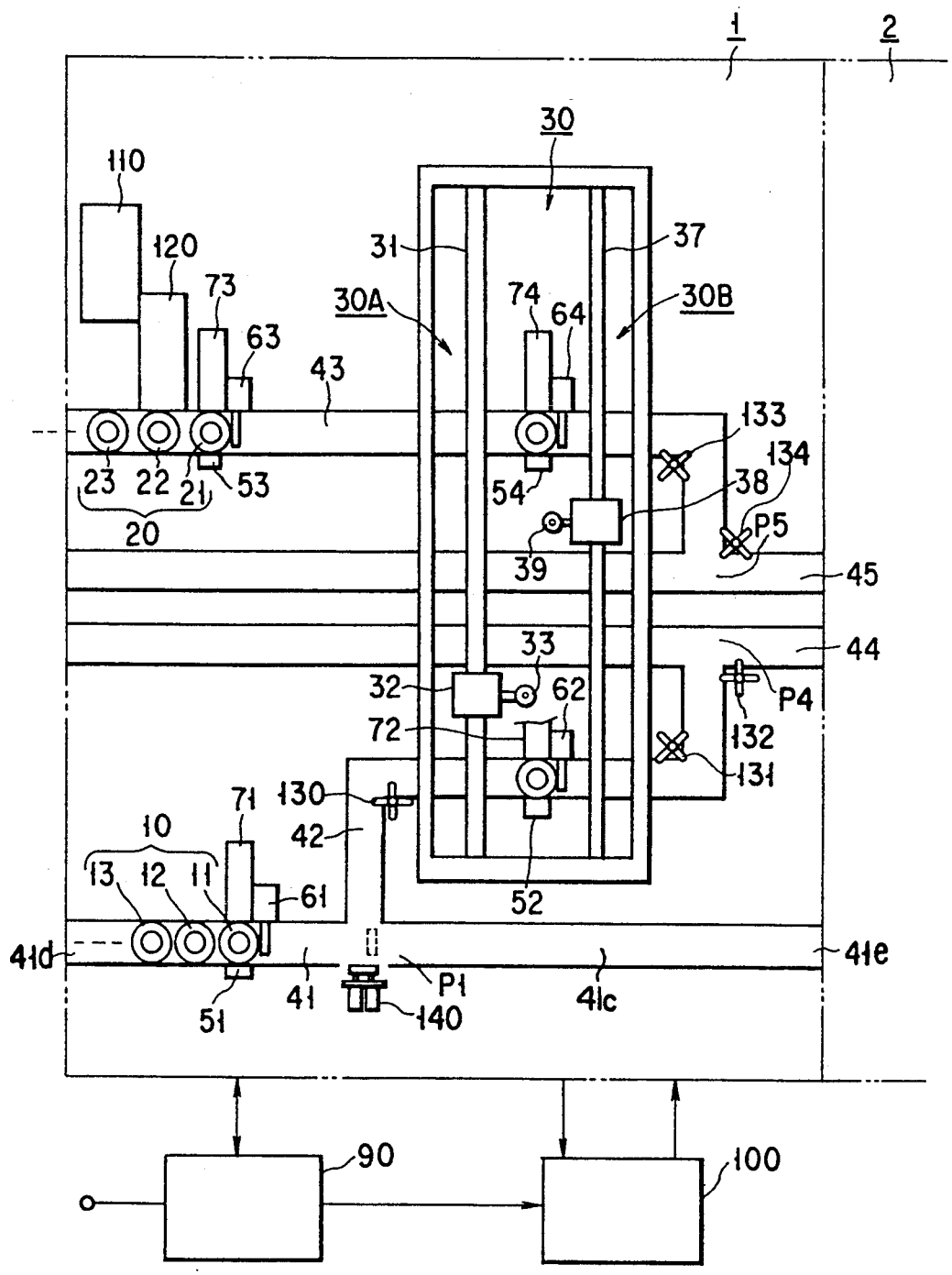
FIG. 1 is a plan view schematically showing a sample sorting apparatus according to the first embodiment of the present invention.

FIG. 1 is a schematic plan view showing a sample sorting apparatus according to the first embodiment of the present invention. Referring to FIG. 1, reference numerals 1 and 2 denote sample sorting apparatuses. The sample sorting apparatuses 1 and 2 respectively is formed as units and are coupled to each other. Although not shown, a plurality of other sample sorting apparatuses are arranged on the right side of the sample sorting apparatus 2 in FIG. 1. In this sample sorting apparatus 1, reference numeral 10 denotes a parent sample containing body group; 20, a child sample containing body group; and 30, a taking up/distributing unit. Reference numerals 41 to 45 denote transport lanes serving as first to fifth transporting means; 51 to 54, vessel detection sensors; 61 to 64, stoppers; 71 to 74, bar code readers for reading sample recognition information; and 130 to 134 and 140, transport direction changeover units. Reference numeral 90 denotes a sample information memory; 100, a sorting controller; 110, a bar code printer; and 120, a label sticking machine. The parent sample containing body group 10 includes parent sample containing bodies 11, 12, 13, . . . . The child sample containing body group 20 includes child sample containing bodies 21, 22, 23 and a large number of other child sample containing bodies (not shown).

The parent sample containing bodies 11, 12, 13, . . . have the same structure. The parent sample containing bodies 11 and 12 are shown as representatives in FIGS. 2 and 3. More specifically, the parent sample containing bodies 11 and 12 is formed of parent sample vessels 11T and 12T, comprising test tubes having neck portions adhered with the bar code labels 11a and 12a on which sample recognition information is printed as a bar code, held in cylindrical holders 11H and 12H, respectively. Two annular groove portions R1 and R2 are formed in the outer circumferential surface of each of the holders 11H and 12H. The respective groove portions R1 are engaged with guide rails 41a and 41b (to be described later), and the respective groove portions R2 are engageable with the stoppers 61 to 64 (to be described later).

Referring back to FIG. 1, the respective child sample containing bodies 21, 22, 23, . . . have the same arrangements as those of the parent sample containing bodies 11, 12, 13, . . . . The respective child sample containing bodies 21, 22, 23, . . . are empty in the initial state.

The taking up/distributing unit 30 is arranged at the taking up/distributing operation area located at almost the central portion in the sample sorting apparatus 1 and has a pair of taking up/distributing mechanisms 30A and 30B. The first taking up/distributing mechanism 30A has a guide bar 31 arranged to be perpendicular to the first and third transport lanes 41 and 43, and a suction unit body 32 slidable along the guide bar 31. The suction unit body 32 has a suction tool 33 for drawing the sample (a liquid or the like) in the sample vessel by suction and discharging the drawn sample. As shown in FIG. 4, the suction tool 33 is constituted by a pipe 34 having one end connected to an air suction unit (not shown) provided in the suction unit body 32, a cylindrical tip mounting plug 35 mounted to the other end of the pipe 34 and made of an elastic member with a through hole formed therein, and a disposable tip 36 mounted on the outer circumferential surface of the tip mounting plug 35.

Referring back to FIG. 1, the second taking up/distributing mechanism 30B also has the same arrangement as that of the first taking up/distributing mechanism 30A. Reference numeral 37 denotes a guide bar; 38, a suction unit body; and 39, a suction tool. The suction tools 33 and 39 are supported at horizontally deviated positions so that the suction unit bodies 32 and 38 can avoid each other when they pass by each other. Also, the suction tools 33 and 39 can be moved downward into the sample vessels in taking up and distributing operations.

The first to fifth transport lanes 41 to 45 have an arrangement as indicated by the sample sorting apparatus 1 as the representative in FIG. 2. More specifically, the first transport lane 41 is formed of a belt conveyor 41c for holder transport, and guide rails 41a and 41b. The guide rails 41a and 41b are engaged with the groove portions R1 of the holders 11H and 12H so that they can guide the holders 11H and 12H holding the parent sample vessels 11T and 12T by stable transport without inverting the holders 11H and 12T.

Referring back to FIG. 1, the first transport lane 41 sequentially transports the respective parent sample containing bodies 11, 12, 13, . . . fed by a parent sample vessel supplying means (not shown) connected to one end portion of the apparatus 1, including the parent sample vessels 11T and 12T, a parent sample vessel 13T, not shown, and the like containing the parent samples, from its inlet end portion 41d on the left side in FIG. 1 into the apparatus body, and then feeds and transports the respective parent sample containing bodies 11, 12, 13, . . . to the outside of the apparatus from its outlet end portion 41e. A parent sample containing body which is discharged to the outside of the apparatus is fed into the first transport lane of the sample sorting apparatus 2.

The vessel detection sensor 51 and the stopper 61 are provided in the vicinity of the inlet of the first transport lane 41. The vessel detection sensor 51 detects arrival of the parent sample containing bodies 11, 12, 13, . . . . The stopper 61 temporarily stops transport of the parent sample containing bodies 11, 12, 13, . . . by a signal from the vessel detection sensor 51. The bar code reader 71 is also provided in the vicinity of the inlet of the first transport lane 41 to read the bar code labels 11a and 12a, a bar code label 13a (not shown), and the like attached to the parent sample vessels 11T, 12T, 13T, . . . (which is not shown) containing bodies 11, 12, 13, . . . that are temporarily stopped by the stopper 61. Since the bar code labels 11a, 12a, 13a, . . . are provided to encircle the respective parent sample vessels 11T, 12T, 13T, . . . they can be read by the bar code reader 71 regardless of directions along which the parent sample containing bodies 11, 12, 13, . . . are set.

The stoppers 61 to 64 have an arrangement as indicated by the stopper 61 as representative in FIGS. 2 and 3. More specifically, the stopper 61 is formed of a stopper body 61a and a stop rod 61b. The stopper body 61a comprises an air-piston/cylinder-device or the like which is provided on the outer side of the guide rail 41b and which moves a stop rod 61 back and forth in a direction perpendicular to the traveling direction of the belt conveyor 41c. The stop rod 61b is provided at the distal end of the stopper body 61a, and projects onto the belt conveyor 41c as required through a hole portion formed in the guide rail 41b in response to the movement of the stopper body 61a so as to be engaged with the groove portion R2 of either holder (11H, 12H, 13H, . . . ), thereby temporarily stopping parent sample containing bodies following an arbitrary one of the parent sample containing bodies 11, 12, 13, . . . .

Figure 7:
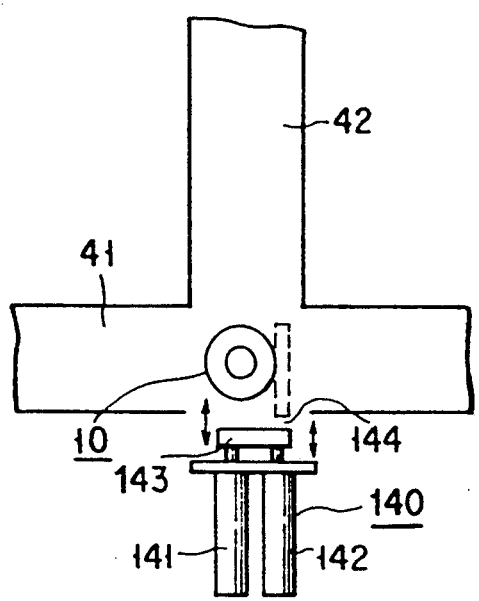
FIG. 7 is a plan view showing another arrangement of a transport direction change-over unit of the sample sorting apparatus according to the first embodiment of the present invention.
Figure 8:
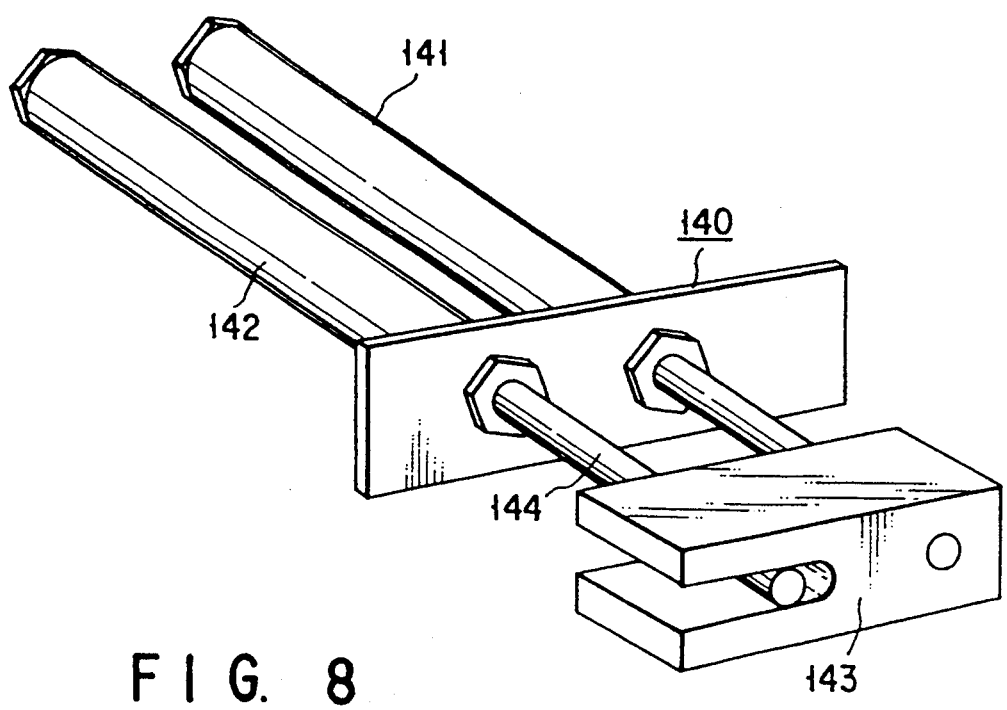
FIG. 8 is a perspective view showing the other arrangement of the transport direction change-over unit of the sample sorting apparatus according to the first embodiment of the present invention.

Referring back to FIG. 1, a branch portion P1 for branching out the second transport lane 42 (to be described later) from 41 is provided midway along the first transport lane 41. The transport direction changeover unit 140 as shown in FIGS. 7 and 8 is provided at the branch portion P1. The transport direction changeover unit 140 has a pushout cylinder 141 and a stopper cylinder 142 that are arranged parallel to each other. The pushout cylinder 141 and the stopper cylinder 142 is operated to be perpendicular to the transport direction of the first transport lines 41. The pushout cylinder 141 is located in the upstream of the first transport lanes of in the transport direction. A pushout tool 143 which projects into the transport lane upon operation of the pushout cylinder 141 is provided at the distal end of the rod piston. The pushout tool 143 has a rectangular parallelpiped shape and is formed with a notched portion 143a communicating with a stopper 144 (to be described later). The stopper 144 which projects into the transport lane over the pushout tool 143, upon operation of the stopper cylinder 142, to be engaged with the parent and child sample containing bodies is provided at the distal end of the stopper cylinder 142.

With the transport direction change-over unit 140 having the arrangement as described above, when the parent sample containing bodies 11, 12, 13, ... are transported to it, it may operate the stopper cylinder 142 to stop these above-described containing bodies by the stopper 144. Subsequently, the pushout cylinder 141 can be operated to push out the containing bodies stopped by the stopper 144, thereby smoothly changing the transport direction.

Upon reception of an instruction from the sorting controller 100, the transport direction change-over unit 140 operates at the branch portion P1 on the belt conveyor 41c at a predetermined timing, thereby transferring at the branch portion P1 a predetermined parent sample containing body of the parent sample containing body group 10 from the first transport lane 41 to the second transport lane 42.

The second transport lane 42 is connected to the first transport lane 41 to be perpendicular to it, and receives the predetermined parent sample containing bodies 11, 12, 13, ... from the first transport lane 41.

The second transport lane 42 is bent at 90° to be parallel to the first transport lane 41, extends via the taking up/distributing unit 30, is bent at 90° again, and merges into the fourth transport lane 44 (to be described later) to be perpendicular to it.

A portion of the second transport lane 42 that passes through the operation area of the taking up/distributing unit 30 is provided with the sensor 52, the stopper 62, and the bar code reader 72. The sensor 52 detects arrival of the parent sample containing bodies 11, 12, 13, .... The stopper 62 temporarily stops transport of the parent sample containing bodies 11, 12, 13, ... upon reception of a signal from the sensor 52. The bar code reader 72 reads the bar code labels 11a, 12a, 13a, ... attached to the parent sample vessels 11T, 12T, 13T, ... containing bodies 11, 12, 13, ... are temporarily stopped by the stopper 62. The transport direction change-over units 130 to 132 are respectively provided at portions of the second transport lane 42 described above that are bent at 90° and at merge portion of the fourth transport lane 44.

The third transport lane 43 transports the child sample containing bodies 21, 22, 23, ... which are supplied from a child sample vessel supplying means (not shown) connected to one end portion of the apparatus 1 and which comprise empty child sample vessels and holders, into the sample sorting apparatus 1, passes via the operation area of the taking up/distributing unit 30, and merges into the fifth transport lane 45 (to be described later) to be perpendicular to it.

The bar code printer 110 and the label sticking machine 120 are provided in the vicinity of the inlet of the third transport lane 43. The bar code printer 110 encodes the sample recognition information into a bar code on the basis of information set and stored in the sample information memory 90 (to be described later) and prints the bar code on labels. The label sticking machine 120 adheres the bar code labels printed by the bar code printer 110 to predetermined portions of, e.g., child sample vessels 21T, 22T, 23T, ... (none are shown) containing bodies 21, 22, 23, ....

The sensor 53, the stopper 63, and the bar code reader 73 are provided adjacent to the label sticking machine 120. The sensor 53 detects arrival of the child sample containing bodies 21, 22, 23, .... The stopper 63 temporarily stops transport of the child sample containing bodies 21, 22, 23, ... in response to a signal from the sensor 53. The bar code reader 73 reads the bar code labels attached to the child sample vessels 21T, 22T, 23T, ... containing bodies 21, 22, 23, ... that are temporarily stopped by the stopper 63.

The sensor 54, the stopper 64, and the bar code reader 74 are provided at a portion of the third transport lane 43 that passes the operation area of the taking up/distributing unit 30. The sensor 54 detects arrival of the child sample containing bodies 21, 22, 23, .... The stopper 64 temporarily stops transport of the child sample containing bodies 21, 22, 23, ... in response to a signal from the sensor 54. The bar code reader 74 reads the bar code labels attached to the child sample vessels 21T, 22T, 23T, ... containing bodies 21, 22, 23, ... that are temporarily stopped by the stopper 63. The transport direction change-over units 133 and 134 are provided at the above-described portion of the third transport lane 43 which is bent at 90° and at merge portion of the fifth transport lane 45.

The fourth transport lane 44 feeds and transports the parent sample containing body group 10, including parent sample vessels that have completed taking up by another sample sorting apparatus, through one inlet end portion of the sample sorting apparatus 1 into the apparatus body, and feeds and transports the parent sample containing body group 10 through the other outlet end portion to the outside of the apparatus body. A merge portion P4 where the first transport lane 41 merges is provided midway along the fourth transport lane 44.

The fifth transport lane 45 feeds and transports the child sample containing body group 20, including child sample vessels that have completed distribution by another sample sorting apparatus, through one inlet end portion of the sample sorting apparatus 1 into the apparatus body, and feeds and transports the child sample containing body group 20 through the other outlet end portion to the outside of the apparatus body. A merge portion P5 where the third transport lane 43 merges is provided midway along the fifth transport lane 45.

The inlets of the first, fourth, and fifth transport lanes 41, 44, and 45 of the sample sorting apparatus 1 can be detachably coupled to the outlets of the corresponding transport lanes of another apparatus. The outlets of the respective transport lanes of the sample sorting apparatus 1 can be detachably coupled to the respective inlets of the corresponding transport lanes of another apparatus.

Processing information, e.g., a required number of times of distributing operations, a required distributing amount, and the like of the respective parent samples, is preset and stored in the sample information memory 90, and can be read as required. The sorting controller 100 controls transport of the parent and child sample containing body groups 10 and 20 and operation of the taking up/distributing unit 30 based on the sample information stored in the sample information memory 90 and the sample recognition information read by the bar code readers 71 to 74.

Figure 5:
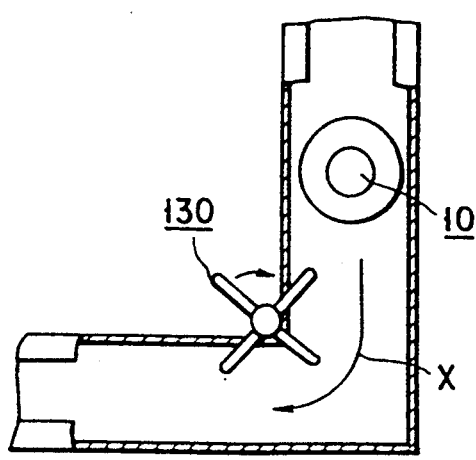
FIG. 5 is a plan view showing an arrangement of a transport direction change-over unit of the sample sorting apparatus according to the first embodiment of the present invention.
Figure 6:
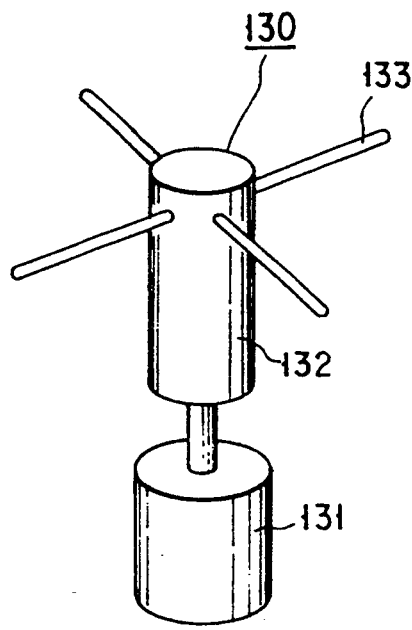
FIG. 6 is a perspective view showing the arrangement of the transport direction change-over unit of the sample sorting apparatus according to the first embodiment of the present invention.

As shown in FIGS. 5 and 6, the transport direction change-over unit 130 has a motor 131, a columnar attachment tool 132, and four elastic rubber rods 133. The motor 131 is provided under the lane by notching the inner rail of the transport direction change-over unit 130. The columnar attachment tool 132 is mounted to the shaft of the motor 131 to be located in the lane. The four elastic rubber rods 133 are mounted to the attachment tool 132 perpendicularly to the shaft of the motor and arranged at an angular interval of 90°. When transport of the parent sample conveying body group 10 is in a direction indicated by an arrow X in FIG. 5, this transport direction change-over unit 130 is rotated clockwise.

The transport direction change-over unit 130 having the arrangement as described above can smoothly change the transport direction when the parent sample conveying bodies 11, 12, 13, . . . and the child sample conveying bodies 21, 22, 23, . . . are transported thereto.

In the sample sorting apparatus having the arrangement as described above, the sample taking up/distributing operation is performed in the following manner. As the preparation for activating the apparatus, an appropriate number of sample sorting apparatuses are provided in accordance with a required distributing amount, and the like of the respective parent samples. The inlets of the first, fourth, and fifth transport lanes 41, 44, and 45 of the respective apparatuses are coupled to the outlets of the corresponding transport lanes of other adjacent apparatuses, and the outlets of the respective transport lanes of the respective apparatuses are coupled to the respective inlets of the corresponding transport lanes of other adjacent apparatuses.

The inlets of the third transport lanes 43 of the respective sample sorting apparatuses are connected to an empty vessel supplying unit (not shown) for supplying empty child sample vessels. The inlet of the first transport lane 41 of the sample sorting apparatus located at the most upstream portion (e.g., the apparatus 1) is connected to a parent sample vessel supplying unit for supplying parent sample vessels. The outlet of the fourth transport lane 44 of the sample sorting apparatus located at the most downstream portion (e.g., another apparatus 2 if only two apparatuses are connected) is connected to a parent sample vessel recovering unit for recovering parent sample vessels that have completed taking up, and the outlet of the fifth transport lane 45 of this apparatus is connected to a child vessel recovering unit for recovering child sample vessels that have completed distribution.

When the entire sample sorting system comprising the plurality of sample sorting apparatuses thus connected is operated, the parent sample containing bodies 11, 12, 13, . . . holding the respective parent sample vessels are sequentially fed from the parent sample vessel supplying unit into the apparatus 1 by the first transport lane 41. When the first parent sample containing body 11, of the fed parent sample containing body group 10, is transported to a predetermined position, attrival of this parent sample containing body 11 is detected by the vessel detection sensor 51 to operate the stopper 61. Thus, travel of the parent sample containing body 11 is temporarily stopped by engaging 61 with groove. It is to be noted that the 41 is kept moving. The bar code of the bar code label 11a attached to the parent sample vessel 11T is read by the bar code reader 71, and sample recognition information is input to the sorting controller 100 based on this bar code. The sorting controller 100 reads information, e.g., the number of times of the distributing operations, the amount of distribution, and the like of the respective parent samples stored in the sample information memory 90 in advance based on the sample recognition information. The sorting controller 100 thus sequentially controls transport of the respective containing bodies 11 to 13 and the operation of the taking up/distributing unit 30 based on the sample recognition information.

After reading the sample recognition information, the stopper 61 is released so that the parent sample containing bodies 11, 12, 13, . . . resume movement. The controller 100 sends out a control signal upon elapse of a given period of time corresponding to a distance between the 61 and P1 and the conveying speed after the release of the stopper 61. Therefore, when the first parent sample containing body 11 reaches the branch portion P1, the transport direction change-over unit 140 is operated based on the control signal and the parent sample containing body 11 is transferred from the first transport lane 41 to the second transport lane 42. When the parent sample containing body 11 that has been transferred to the second transport lane 42 is transported to the taking up/distributing unit 30, it is detected by the sensor 52 and is temporarily stopped by the stopper 62. The bar code of the bar code label 11a attached to the percent sample vessel 11T is read by the bar code reader 72.

The child sample containing bodies 21, 22, 23, . . . holding the empty child sample vessels 21T, 22T, 23T, . . . are fed into the apparatus body by the third transport lane 43. Simultaneously, based on the control signal from the sorting controller 100, the bar code printer 110 is operated to encode the sample recognition information corresponding to the parent sample in the parent sample vessel 11T into a bar code, and to print it on bar code labels. These bar code labels are adhered to the predetermined portions of the supplied empty child sample vessels 21T, 22T, 23T, . . . by the label sticking machine 120. The child sample containing bodies 21, 22, 23, . . . comprising the empty child sample vessels 21T, 22T, 23T, . . . are detected by the sensor 53 and temporarily stopped by the stopper 63. The bar code reader 73 checks whether or not the sample recognition information of the bar code is accurate. If the bar code reader 73 determines that the bar code is accurate, the stopper 63 is canceled. Hence, the child sample containing bodies 21, 22, 23, . . . comprising the child sample vessels are transported to the taking up/distributing unit 30 by the third transport lane 43 and temporarily stopped at the predetermined position by the stopper 64. The bar code of the bar code label attached to the child sample vessel 21T to 23T are read by the bar code reader 74, and the bar code reader 74 checks whether or not the sample recognition information of the bar code is accurate. As a result, the parent sample can be always distributed into the child sample vessel having the correct bar code.

The taking up/distributing unit 30 performs the taking up/distributing operation in the following manner. More specifically, in the first taking up/distributing mechanism 30A, the distal end of the suction tool 33 mounted to the suction unit body 32 is inserted in the parent sample vessel 11T of the stopped parent sample containing body 11. Subsequently, the air suction unit is operated to draw a predetermined amount of the sample by suction, the amount being determined based on the sample recognition information, and holds it. The suction tool 33 is then pulled out and moved to a position above the child sample vessel 21T of the first child sample containing body 21 which is temporarily stopped by the stopper 64. Then, the suction unit is operated in the opposite direction to discharge and distribute the parent sample in the suction tool 33 into the child sample vessel 21T in an amount determined based on the information of the sample information memory 90. The taking up/distributing operation is performed in the same manner by the second taking up/distributing mechanism 30B as well. However, note that the distributing operation by the second taking up/distributing mechanism 30B is performed for the second child sample vessel 22T. The distributing operation for a number of child sample vessels, the number being determined based, on the sample recognition information is performed in this manner. The timings of the first and second taking up/distributing mechanisms 30A and 30B are shifted by half the cycle. Therefore, if the taking up operation is performed by the first taking up/distributing mechanism 30A, the distributing operation is performed by the second taking up/distributing mechanism 30B.

When the taking up/distributing operation is completed, the stopper 62 is canceled, and transport of the parent sample containing body 11 having the parent sample vessel 11T that has completed taking up is resumed. The parent sample containing body 11 transported to the merge portion P4 is merged with the fourth transport lane 44, and is fed to the outside of the apparatus 1 through the outlet of the fourth transport lane 44. Meanwhile, the stopper 64 is canceled, and the child sample containing bodies 21, 22, 23, . . . , holding the child sample vessels 21T, 22T, 23T, . . . that have completed distribution resume transport. The child sample containing bodies 21, 22, 23, . . . transported to the merge portion P5 are merged with the fifth transport lane 45 and fed out to the outside of the apparatus 1 through the outlet of the fifth transport lane 45.

If, e.g., the parent sample containing body 12 is not transported to the second transport lane 42 by the transport direction change-over unit 140 upon reception of the control signal from the sorting controller 100, this parent sample containing body 12 is directly fed out to the outside of the apparatus through the first transport lane 41. The parent sample containing body 12 discharged out to the outside of the apparatus is then fed into the adjacent sample sorting apparatus 2 through the inlet of the first transport lane 41 thereof, and subjected to the same process as that of the sample sorting apparatus 1 described above almost simultaneously.

In this manner, the apparatus of this embodiment is basically a separate type sample sorting apparatus for separately controlling each parent sample vessel. Therefore, even if the respective parent samples are to be distributed to correspond to different numbers of inspection items, the number of child sample vessels 21T, 22T, 23T, . . . will not become excessive or short, so that an efficient distributing operation can be performed. Since all the operations are automatically controlled by the sample information memory 90 and the sorting controller 100, the sample will not touch the human body to get contaminated, and the distributing operation can be performed quickly and reliably. In the taking up/distributing unit 30, since the taking up operation and the distributing operation are alternately performed by the pair of taking up/distributing mechanisms 30A and 30B with a time lag of half the cycle, the taking up/distributing time is shortened, thereby improving the processing speed.

According to this embodiment, since a plurality of sample sorting apparatuses respectively constituting units are arranged, and the first, fourth, and fifth transport lanes of the respective apparatuses are connected in series, the sample taking up/distributing operation can be performed in the interlocked manner. Thus, work loads can be uniformly applied to the respective apparatuses, thereby increasing the efficiency of the sorting/distributing operation. Even when one sample sorting apparatus, e.g., the taking up/distributing unit 30 of the apparatus 1 breaks down, if the transport direction change-over unit 140 of this apparatus 1 is not operated, the parent sample containing bodies 11, 12, 13, . . . are fed into the next sample sorting apparatus 2 as long as the first transport lane 41 operates. Therefore, even when a trouble occurs in one apparatus, the operation of the system as a whole will not be stopped but can be continued. Since the apparatus of this embodiment is of a unit type, the number of units to be connected may be increased or decreased in accordance with the necessary sample processing amount, and the design of the sample sorting apparatus need not be altered in accordance with an increase/decrease in the sample processing amount, unlike in the conventional apparatus.

The embodiment described above uses the second transport lane 42 which is bent in a crank manner. However, the first and third transport lanes 41 and 43 may be linearly connected.

Figure 9:
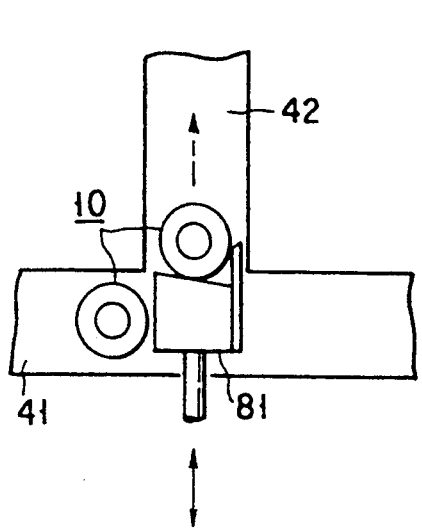
FIG. 9 is a plan view showing still another arrangement of a transport direction change-over unit of the sample sorting apparatus according to the first embodiment of the present invention.
Figure 10:
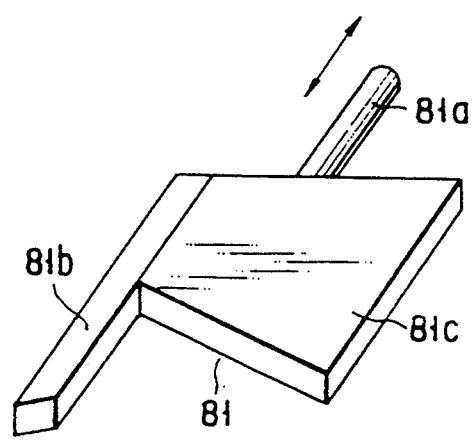
FIG. 10 is a perspective view showing the arrangement (FIG. 9) of the transport direction change-over unit of the sample sorting apparatus according to the first embodiment of the present invention.

The above embodiment uses transport direction change-over units as shown in FIGS. 5 to 8. However, transport direction change-over units 81 as shown in FIGS. 9 and 10 may be arranged in place of the transport direction change-over units 130 to 134 and 140, outside the portions of the first, second and third transport lanes 41 to 43 where the transport direction is changed at the right angle.

The transport direction change-over unit 81 is formed of a rod-shaped member 81a and holding members 81b and 81c. The rod-shaped member 81a is connected to a cylinder (not shown) and perpendicular to the transport direction of the first transport lane 41. The members 81b and 81c are provided at the distal end of the rod-shaped member 81a and hold the parent sample containing body. The transport direction change-over unit 81 is provided on the outer side of the guide rail 41b of the first transport lane 41 and moves forward and backward in a direction perpendicular to the traveling direction of the belt conveyor 41c.

The present invention is not limited the embodiments described above, and various changes and modifications may be made without departing from the spirit and scope of the invention.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A sample sorting apparatus comprising:

first conveying means for conveying a parent sample vessel containing a parent sample along a first convey path, said first convey path comprising a branch path;

means for taking up the parent sample from said parent sample vessel conveyed by said first conveying means;

sample recognition information reading means for reading sample recognition information attached to said parent sample vessel;

second conveying means for conveying child sample vessels along a second convey path; and means for distributing the parent sample took up by said taking up means into a number of child sample vessels in accordance with sample recognition information read by said reading means.

2. An apparatus according to claim 1, in which said taking up means comprises first means for temporarily stopping said parent sample vessels in order to taking up, and said distributing means comprises second means for temporarily stopping said child sample vessels to distribute the parent sample.

3. An apparatus according to claim 1, in which said second convey path comprises a branch path.

4. An apparatus according to claim 1, in which said taking up means comprises a pipe, suction means provided at one end of said pipe, tip mounting means provided at the other end of said pipe, and a disposable tip mounted to said tip mounting means.

5. An apparatus according to claim 1, in which said distributing means comprises a pipe, discharging means provided at one end of said pipe, tip mounting means provided at the other end of said pipe, and a disposable tip mounted to said tip mounting means.

6. An apparatus according to claim 1, in which said taking up means and said distributing means comprise two pairs, and one and the other pairs of said taking up means and said distributing means alternately perform an operation of taking up the parent sample from said parent sample vessels and an operation of distributing the took up parent sample into said child sample vessels.

7. A sample sorting system comprising:
(a) first, second and third sample sorting units;
(b) each said unit including:
(i) first transporting means for feeding and transporting a parent sample vessel, containing a parent sample and attached with sample recognition information, into an apparatus body, said first transporting means including an outlet;
(ii) second transporting means for transporting said parent sample vessel, fed and transported to said apparatus body by said first -transporting means, to a taking up/distributing operation area;
(iii) means for supplying empty child sample vessels attached with sample recognition information of a sample to be distributed;
(iv) third transporting means for transporting said child sample vessels supplied by said supplying means to said taking up/distributing operation area;
(v) a taking up/distributing unit, provided at said taking up/distributing operation area, for taking up a parent sample from said parent sample vessel transported to said operation area, and distributing the took up parent sample into said empty child sample vessels transported to said operation area;
(vi) fourth transporting means for feeding and transporting said parent sample vessels to an outlet from said sorting unit after a taking up operation therefrom by said taking up/distributing unit has completed;
(vii) fifth transporting means for feeding and transporting said child sample vessels to an outlet from said sorting unit after a distributing operation thereto by said taking up/distributing unit has completed;
(viii) transport stopping means, provided along a portion of at least one of said first to fifth transporting means, for temporarily stopping transport of said sample vessels upon detection of arrival of said sample vessels; and
(ix) sample recognition information reading means for reading sample recognition information attached to said respective sample vessels, transport of which has been stopped by said transport stopping means; and
(c) control means for said sorting units for controlling transport of said parent sample vessels and said child sample vessels and operation of said taking up/distributing unit based on the sample recognition information read by said sample recognition information reading means and preset operational information;

said first, fourth, and fifth transporting means in said second and third units having inlets for coupling with outlets of said first, fourth and fifth transporting means of said first and second units.

8. An apparatus according to claim 7, in which said taking up/distributing unit alternatively performs an operation of taking up the parent sample from said parent sample vessel and an operation of distributing the took up parent sample into said child sample vessels by a pair of taking up/distributing mechanisms.

9. An apparatus according to claim 7, in which said sample recognition information is a bar code.

10. An apparatus according to claim 7, in which said parent sample vessel is held by a conveying body.

11. An apparatus according to claim 7, in which said child sample vessels are held by conveying bodies.

12. An apparatus according to claim 7, in which said first to fifth transporting means comprise guide rails and belt conveyors.

13. A sample sorting system comprising: a first sample taking up/distributing unit including a first parent sample vessel supply port to be connected to means for supplying a parent sample vessel containing a parent sample, a first child sample vessel supply port to be connected to first child sample vessel supply means, and a first parent sample vessel discharge port for discharging said parent sample vessel; and a second sample taking up/distributing unit including a second parent sample vessel supply part to be connected to said first parent sample vessel discharge port, a second child sample vessel supply port to be connected to second child sample vessel supply means, and a second parent sample vessel discharge port for discharging said parent sample vessel, said first sample taking up/distributing unit comprising first conveying means, connected to said first parent sample vessel supply port, for conveying said parent sample vessel along a first convey path, first taking up means for taking up a parent sample from said parent sample vessel conveyed by said first conveying means, first discharging means for discharging said parent sample vessel, containing a parent sample that is not took up by said first taking up means, to said first parent sample vessel discharge port, second conveying means, connected to said first child sample vessel supply port, for conveying child sample vessels along a second convey path, and first distributing means for taking up the parent sample took up by said first taking up means into said child sample vessels in accordance with sample recognition information read by reading means, and said second sample taking up/distributing unit comprising third conveying means, connected to said first parent sample vessel discharge port, for conveying said parent sample vessel containing parent sample that is not took up by said first taking up means along a third convey path, second taking up means, for taking up the parent sample from said parent sample vessel conveyed by said third conveying means, third discharging means for discharging said parent sample vessel, containing a parent sample that is not took up by said second taking up means, to said second parent sample vessel discharge port, fourth conveying means, connected to said second child sample vessel supply port, for conveying said child sample vessels along a fourth convey path, and means for taking up the parent sample took up by said second taking up means into said child sample vessels conveyed by said fourth conveying means.

14. A sample sorting system comprising: a first sample taking up/distributing unit including a first parent sample vessel supply port to be connected to means for supplying parent sample vessel containing a parent sample, a first child sample vessel supply port to be connected to first child sample vessel supply means, a first parent sample vessel discharge port for discharging said parent sample vessel, and a first child sample vessel discharge port for discharging first child sample vessels; and a second sample taking up/distributing unit including a second parent sample vessel supply port to be connected to said first parent sample vessel discharge port, a second child sample vessel supply port to be connected to said first child sample vessel discharge port, a second parent sample vessel discharge port for discharging said parent sample vessel, and a second child sample vessel discharge port for discharging said child sample vessels, said first sample taking up/distributing unit comprising first conveying means, connected to said first parent sample vessel supply port, for conveying said parent sample vessel along a first convey path, first taking up means for taking up a parent sample from said parent sample vessel conveyed by said first conveying means, first discharging means for discharging said parent sample vessel, containing parent sample that is not took up by said first taking up means, to said first parent sample vessel discharge port, second conveying means, connected to said first child sample vessel supply port, for conveying child sample vessels along a second convey path, and first distributing means for taking up the parent sample took up by said first taking up means into said child sample vessels in accordance with sample recognition information read by reading means, and said second sample taking up/distributing unit comprising third conveying means, connected to said first parent sample vessel discharge port, for conveying said parent sample vessel containing parent sample that is not took up by said first taking up means along a third convey path, second taking up means for taking up the parent sample from said parent sample vessel conveyed by said third conveying means, third discharging means for discharging said parent sample vessel, containing a parent sample that is not took up by said second taking up means, to said second parent sample vessel discharge pod, fourth conveying means, connected to said second child sample vessel supply pod, for conveying said child sample vessels along a fourth convey path, and means for taking up the parent sample took up by said second taking up means into said child sample vessels conveyed by said fourth conveying means.

* * * * *